United States Patent
Bhirud et al.

(10) Patent No.: US 10,494,342 B2
(45) Date of Patent: Dec. 3, 2019

(54) PROCESS FOR THE PREPARATION OF APREMILAST

(71) Applicant: Glenmark Life Sciences Limited, Solapur (IN)

(72) Inventors: Shekhar Bhaskar Bhirud, Mumbai (IN); Suresh Mahadev Kadam, Thane (IN); Sachin Baban Gavhane, Thane (IN); Sandeep Bandu Khandagale, Thane (IN); Sunil Pandurang Nirgude, Thane (IN); Ajit Shankar Mindhe, Thane (IN); Rajesh Kumar Dwivedi, Navi Mumbai (IN)

(73) Assignee: Glenmark Life Sciences Limited, Solapur (IN)

( * ) Notice: Subject to any disclaimer, the term of this patent is extended or adjusted under 35 U.S.C. 154(b) by 0 days.

(21) Appl. No.: 15/754,067

(22) PCT Filed: Aug. 22, 2016

(86) PCT No.: PCT/IB2016/054998
§ 371 (c)(1),
(2) Date: Feb. 21, 2018

(87) PCT Pub. No.: WO2017/033116
PCT Pub. Date: Mar. 2, 2017

(65) Prior Publication Data
US 2019/0010123 A1    Jan. 10, 2019

(30) Foreign Application Priority Data
Aug. 26, 2015 (IN) .................. 3272/MUM/2015

(51) Int. Cl.
| | |
|---|---|
| *C07D 209/48* | (2006.01) |
| *C07C 69/96* | (2006.01) |
| *C07C 317/28* | (2006.01) |
| *C07C 15/08* | (2006.01) |

(52) U.S. Cl.
CPC ............ *C07D 209/48* (2013.01); *C07C 15/08* (2013.01); *C07C 69/96* (2013.01); *C07C 317/28* (2013.01); *C07B 2200/13* (2013.01)

(58) Field of Classification Search
CPC ....... C07D 209/48; C07C 15/08; C07C 69/96; C07C 317/28
See application file for complete search history.

(56) References Cited

U.S. PATENT DOCUMENTS

| | | | |
|---|---|---|---|
| 2003/0187052 A1 | 10/2003 | Muller et al. | |
| 2008/0234359 A1* | 9/2008 | Muller | A61K 31/4035 514/417 |

FOREIGN PATENT DOCUMENTS

| | | |
|---|---|---|
| CN | 104447443 A | 3/2015 |
| CN | 105330586 A | 2/2016 |
| WO | 2016066116 A1 | 5/2016 |

* cited by examiner

*Primary Examiner* — Joseph R Kosack
(74) *Attorney, Agent, or Firm* — Ryan, Mason & Lewis LLP

(57) ABSTRACT

The present invention relates to a process for preparation of apremilast. The present invention relates to p-xylene solvate of apremilast and process for its preparation.

15 Claims, 4 Drawing Sheets

PROCESS FOR THE PREPARATION OF APREMILAST

PRIORITY

This application claims priority under 35 U.S.C. § 371 to International Application No. PCT/IB2016/054998, filed Aug. 22, 2016 which claims the benefit of Indian Provisional Application 3272/MUM/2015 filed Aug. 26, 2015, and entitled "PROCESS FOR THE PREPARATION OF APREMILAST", the contents of which are incorporated herein by reference.

FIELD OF THE INVENTION

The present invention relates to process for preparation of apremilast.

BACKGROUND OF THE INVENTION

Apremilast, which is chemically known as N-[2-[(1S)-1-(3-ethoxy-4-methoxyphenyl)-2-(methylsulfonyl) ethyl]-2,3-dihydro-1,3-dioxo-1H-isoindol-4-yl]acetamide is represented by a compound of formula I,

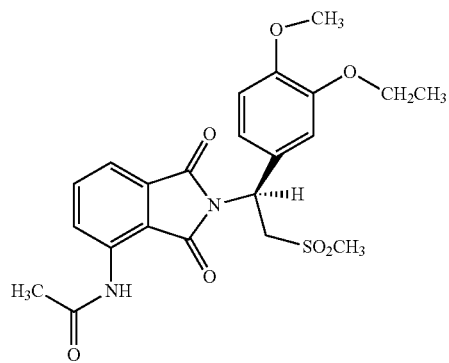

Apremilast marketed as OTEZLA® is a tablet available in multiple strengths for oral administration and is indicated for the treatment of adult patients with active psoriatic arthritis.

Various synthetic processes for preparation of apremilast are known in the art. The present invention provides a process for preparation of apremilast wherein a non-carboxylic acid solvent is used in the condensation of compound of formula II with compound of formula III or salt thereof which provides apremilast with better purity profile and which can be easily performed on industrial scale.

SUMMARY OF THE INVENTION

In one embodiment the present invention provides a process for the preparation of apremilast, a compound of formula I

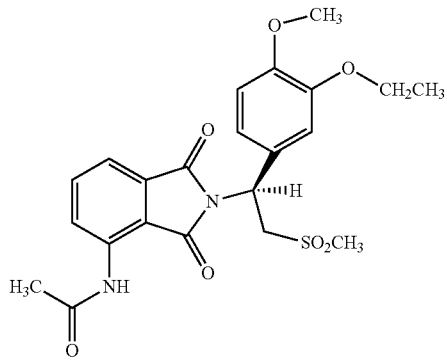

comprising reacting a compound of formula II with a compound of formula III or a salt thereof

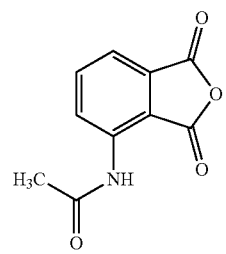

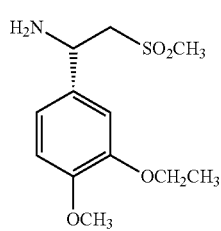

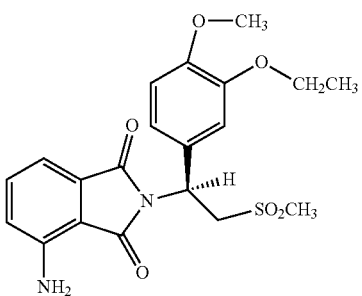

in the presence of a non-carboxylic acid solvent to obtain apremilast wherein the content of deacetyl apremilast, a compound of formula IV is less than 1% w/w as determined by HPLC.

In one embodiment, the present invention provides a method of assessing the purity of apremilast by HPLC comprising the steps of:
a) providing a standard solution of deacetyl apremilast, the compound of formula IV; and
b) using the solution as a reference marker to determine the level of deacetyl apremilast impurity.

In one embodiment, the present invention provides apremilast p-xylene hemisolvate.

In one embodiment, the present invention provides apremilast p-xylene hemisolvate characterized by X-ray Diffraction (XRD) spectrum having peak reflections at about 13.15, 14.92 and 18.89±0.2 degrees 2 theta.

In one embodiment, the present invention provides a process for the preparation of apremilast, a compound of formula I, in amorphous form, the process comprising:
(a) dissolving a solvate of apremilast in a solvent to form a solution; and
(b) removing the solvent from the solution obtained in (a).

In one embodiment, the present invention provides, L-pyroglutamate salt of (S)-2-(3-ethoxy-4-methoxyphenyl)-1-(methyl sulphonyl)eth-2-ylamine characterized by 1HNMR having peaks at 1.32, 1.93-2.29, 2.88, 3.36-3.52, 3.71, 3.96-4.01, 4.335.52, 6.89, 7.05, 7.79.

In one embodiment the present invention provides apremilast,

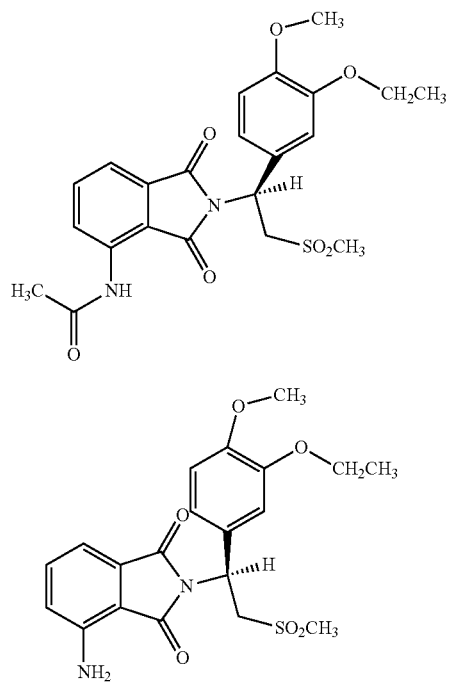

a compound of formula I, wherein content of deacetyl apremilast, the compound of formula IV, is less than 1% w/w as determined by HPLC.

In one embodiment the present invention provides apremilast dimethyl carbonate solvate.

In one embodiment the present invention provides apremilast dimethyl carbonate solvate characterized by Differential Scanning Calorimetric (DSC) thermogram having endothermic peak at about 121° C.±3° C.

DETAILED DESCRIPTION OF THE INVENTION

Figure 1:
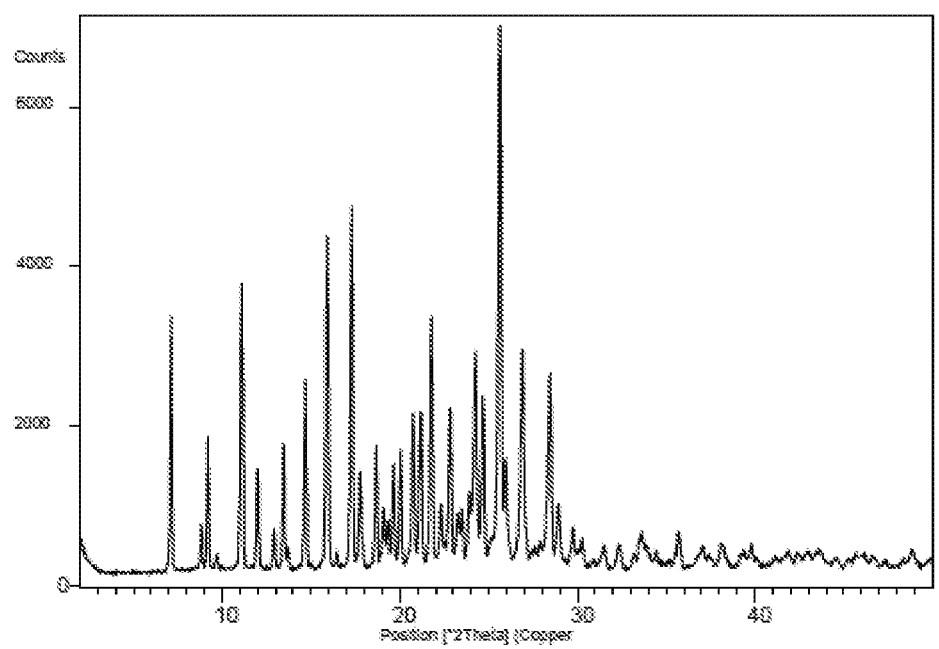
FIG. 1: XRD pattern of apremilast p-xylene hemisolvate according to ex 17.
Figure 2:
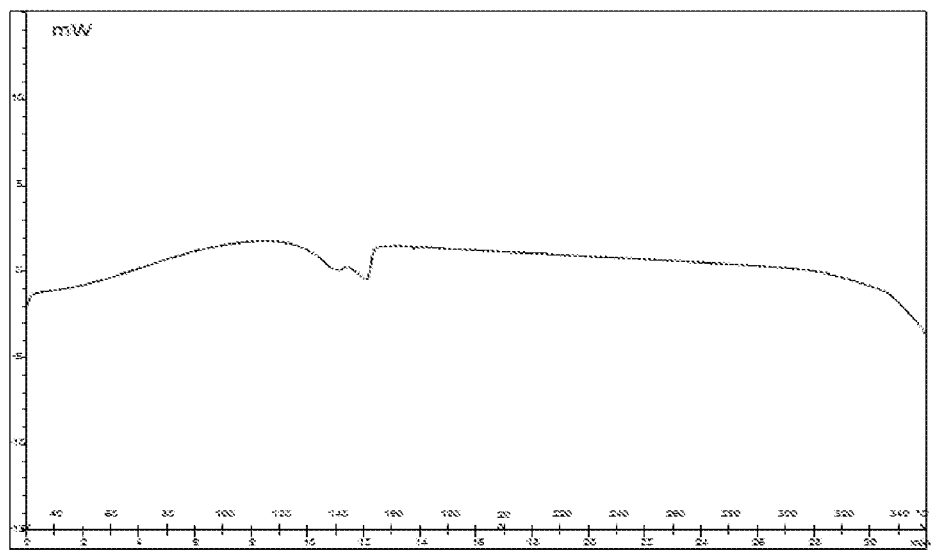
FIG. 2: DSC spectrum of apremilast p-xylene hemisolvate according to ex 17.
Figure 3:
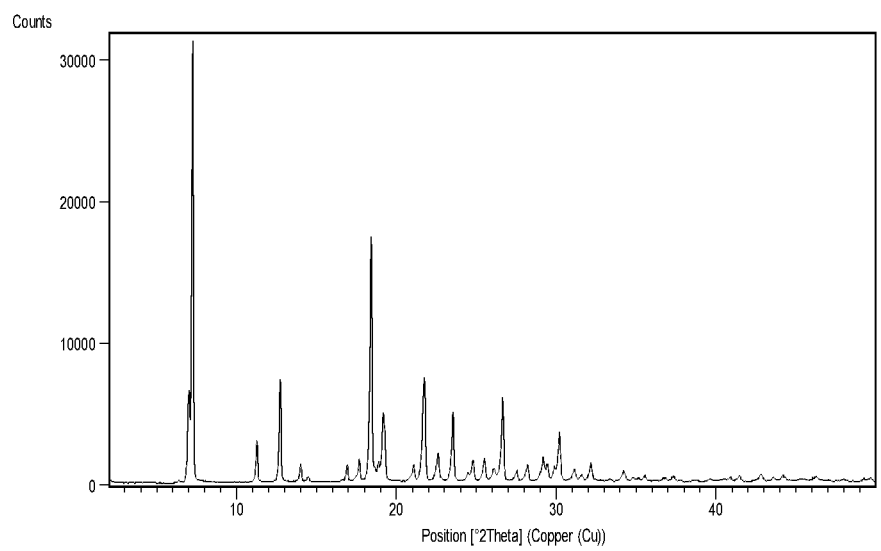
FIG. 3: XRD pattern of L-pyroglutamate salt of (S)-2-(3-ethoxy-4-methoxyphenyl)-1-(methylsulphonyl)eth-2-ylamine according to example 16.
Figure 4:
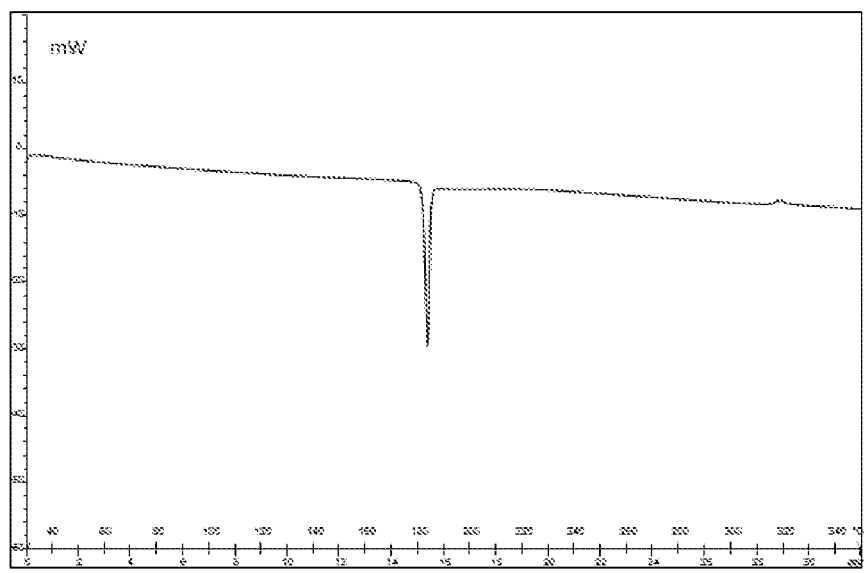
FIG. 4: DSC spectrum of L-pyroglutamate salt of (S)-2-(3-ethoxy-4-methoxyphenyl)-1-(methylsulphonyl)eth-2-ylamine according to example 16.

In one embodiment, the present invention provides a process for the preparation of apremilast, a compound of formula I

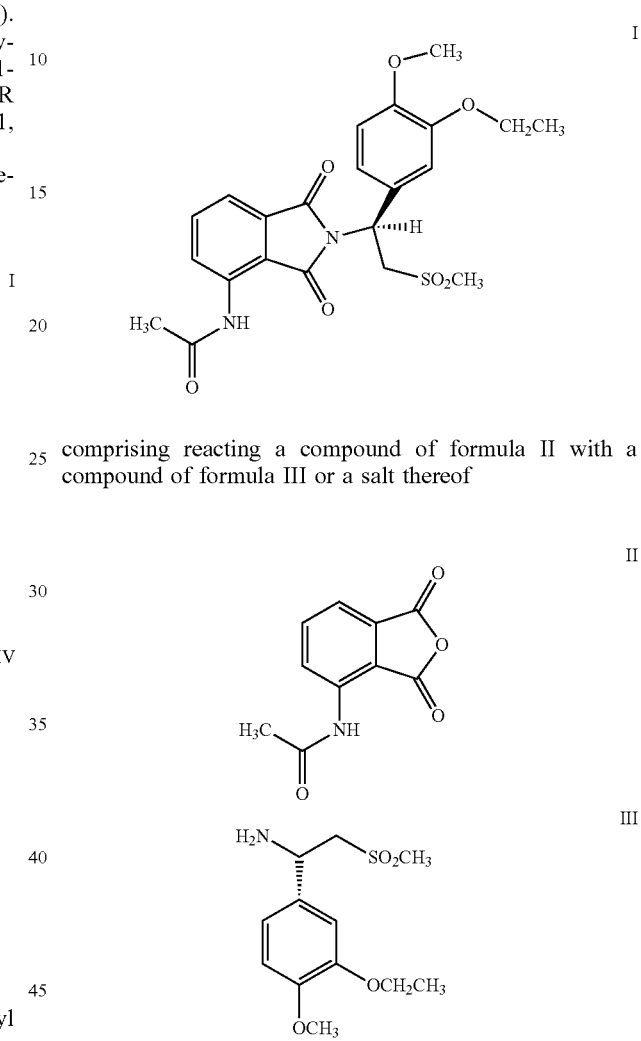

comprising reacting a compound of formula II with a compound of formula III or a salt thereof in the presence of a non-carboxylic acid solvent to obtain apremilast wherein the content of deacetyl apremilast, a compound of formula IV is less than 1% w/w as determined by HPLC.

In one embodiment, the present invention provides a process for the preparation of apremilast, a compound of formula I wherein the reaction of compound of formula II with a compound of formula III or a salt thereof is carried out in absence of acetic acid.

In one embodiment, non-carboxylic acid solvent is a solvent which does not have a carboxylic acid group.

In one embodiment, non-carboxylic acid solvent is any solvent in which the reaction of compound of formula II with compound of formula III or a salt thereof is carried out to obtain apremilast a compound of formula I in high purity.

In one embodiment, the non-carboxylic solvent is selected from the group consisting of an alcohol, a ketone, a hydrocarbon, a halogenated hydrocarbon, amides, sulfoxides, ether, ester, nitriles, water or mixtures thereof.

In one embodiment, the non-carboxylic solvent is selected from the group consisting of an alcohol, a ketone, a halogenated hydrocarbon, amides, sulfoxides, ether, ester, nitriles, water or mixtures thereof.

In one embodiment, an alcohol solvent may be selected from the group consisting of methanol, ethanol, propanol, isopropanol, n-butanol, tert-butanol, cyclohexanol and the like; a ketone solvent may be selected from the group consisting of acetone, methyl ethyl ketone, isopropyl ketone, methyl tert-butyl ketone and the like; a hydrocarbon solvent may be selected from the group consisting of toluene, xylene, cyclohexane, n-heptane, hexane and the like; a halogenated hydrocarbon solvent may be selected from the group consisting of methylene dichloride, ethylene dichloride, chloroform and the like; amide solvent may be selected from the group consisting of dimethyl formamide, dimethyl acetamide, formamide and the like; sulfoxides such as dimethyl sulfoxide and the like; an ether solvent may be selected from the group consisting of diethyl ether, di-isopropyl ether, methyl tert-butyl ether, tetrahydrofuran and the like; esters such as ethyl acetate, butyl acetate, isopropyl acetate and the like; nitriles such as acetonitrile, propionitrile and the like.

In one embodiment, the nitrile solvent is acetonitrile.

In one embodiment the amide solvent is selected from the group consisting of dimethylformamide (DMF), dimethyl acetamide and formamide.

In one embodiment the ketone solvent is selected from the group consisting of acetone, methyl ethyl ketone and methyl isobutylketone.

In one embodiment the solvent is water.

In one embodiment, the present invention provides a process for the preparation of apremilast, a compound of formula I wherein in the reaction of compound of formula II with a compound of formula III or a salt thereof, the salt is selected from the group consisting of an optically active acid or chiral amino acid.

In one embodiment, the optically active acid may be selected from the group consisting of mandelic acid, tartaric acid, camphor sulfonic acid, dibenzoyltartaric acid, di-p-toluoyl tartaric acid, malic acid, aspartic acid, mucic acid, pyroglutamic acid, glucoronic acid, camphoric acid, gluconic acid, lactic acid, pantothenic acid, phenylpropionic acid and diacetyl tartaric acid.

In one embodiment, the chiral amino acid may be selected from the group consisting of alanine, arginine, aspartic acid, glutamine, glutamic acid, glycine, isoleucine, leucine, phenylalanine, proline, serine, valine, 4-aminobutyric acid, 2-amino isobutyric acid, 3-amino propionic acid, norleucine, norvaline, hydroxyproline, cysteic acid, t-butylglycine, t-butylalanine, phenylglycine, cyclohexylalanine, N-acetylphenyl alanine or N-acetyl leucine.

In one embodiment, the present invention provides for the preparation of apremilast comprising reacting the compound of formula II with an optically active acid salt of compound of formula III, wherein the optically active acid is L-pyroglutamate.

In one embodiment, the present invention provides for the preparation of apremilast comprising reacting the compound of formula II with the salt of compound of formula III, wherein the salt of compound III is L-pyroglutamate salt of (S)-2-(3-ethoxy-4-methoxyphenyl)-1-(methylsulphonyl)eth-2-ylamine.

In one embodiment, the present invention provides a process for the preparation of apremilast comprising reacting the compound of formula II with L-pyroglutamate salt of (S)-2-(3-ethoxy-4-methoxyphenyl)-1-(methylsulphonyl)eth-2-ylamine in the presence of a non-carboxylic acid solvent.

In one embodiment, the present invention provides a process for the preparation of apremilast, a compound of formula I comprising, reacting the compound of formula II with the L-pyroglutamate salt of compound of formula III in absence of a carboxylic acid solvent.

In one embodiment, the present invention provides a process for the preparation of apremilast, a compound of formula I comprising, reacting the compound of formula II with the L-pyroglutamate salt of compound of formula III in absence of acetic acid.

In one embodiment, the present invention provides a process for the preparation of apremilast, a compound of formula I comprising reacting the compound of formula II with the L-pyroglutamate salt of compound of formula III in the presence of a non-carboxylic acid solvent wherein the content of deacetyl apremilast, a compound of formula IV is less than 1% w/w as determined by HPLC.

In one embodiment, the present invention provides a process for the preparation of apremilast, a compound of formula I comprising reacting the compound of formula II with the L-pyroglutamate salt of compound of formula III in the absence of acetic acid solvent wherein the content of deacetyl apremilast, a compound of formula IV is less than 1% w/w as determined by HPLC.

In one embodiment, the present invention provides a process for the preparation of apremilast, a compound of formula I comprising reacting the compound of formula II with L-pyroglutamate salt of compound of formula III in the presence of acetonitrile wherein the content of deacetyl apremilast, a compound of formula IV is less than 1% w/w as determined by HPLC.

In one embodiment, the present invention provides a process for the preparation of apremilast, a compound of formula I comprising reacting the compound of formula II with L-pyroglutamate salt of compound of formula III in the presence of acetonitrile wherein the content of deacetyl apremilast, a compound of formula IV is less than 0.5% w/w as determined by HPLC.

In one embodiment, the present invention provides a process for the preparation of compound of formula II with a chiral amino acid salt of compound of formula III, wherein the chiral amino acid is N-acetyl-L-Leucine.

In one embodiment, the present invention provides a process for the preparation of apremilast, a compound of formula I, comprising reacting the compound of formula II with N-acetyl-L-leucine salt of compound of formula III in the presence of a non-carboxylic acid solvent.

In one embodiment, the present invention provides a process for the preparation of apremilast, a compound of formula I, comprising reacting the compound of formula II with N-acetyl-L-leucine salt of compound of formula III in the absence of a carboxylic acid solvent.

In one embodiment, the present invention provides a process for the preparation of apremilast, a compound of formula I comprising, reacting the compound of formula II with the N-acetyl-L-leucine salt of compound of formula III in the absence of acetic acid.

In one embodiment, the present invention provides a process for the preparation of apremilast, a compound of formula I comprising reacting the compound of formula II with the N-acetyl-L-leucine salt of compound of formula III in the presence of a non-carboxylic acid solvent wherein the content of deacetyl apremilast, a compound of formula IV is less than 1% w/w as determined by HPLC.

In one embodiment, the present invention provides a process for the preparation of apremilast, a compound of formula I comprising reacting the compound of formula II with N-acetyl-L-leucine salt of compound of formula III in the presence of acetonitrile wherein the content of deacetyl apremilast, a compound of formula IV is less than 1% w/w as determined by HPLC.

In one embodiment, the present invention provides a process for the preparation of apremilast, a compound of formula I comprising reacting the compound of formula II with N-acetyl-L-leucine salt of compound of formula III in the presence of acetonitrile wherein the content of deacetyl apremilast, a compound of formula IV is less than 0.5% w/w as determined by HPLC.

In one embodiment, the reaction of compound of formula II with the compound of formula III or a salt thereof transpires over a temperature range of about 20° C. to about reflux temp of the solvent. Preferably, the reaction transpires at reflux temp of the solvent.

In one embodiment, apremilast is obtained by the reaction of compound of formula II with the compound of formula III or a salt thereof by removing the solvent and basifying the reaction mass using a suitable base. Apremilast is then isolated by extracting in a suitable solvent followed by removal of solvent.

The solvent may be selected from the group consisting of chlorinated hydrocarbon solvents such as methylene dichloride, ethylene dichloride, chloroform, carbon tetrachloride; ethers such as diethyl ether, methyl tertiary butyl ether, di-isopropyl ether, tetrahydrofuran; nitriles such as acetonitrile, propionitrile; esters such as ethyl acetate, butyl acetate, isopropyl acetate; hydrocarbons such as, cyclohexane, toluene, xylene, hexane; alcohols such as methanol, ethanol, butanol, isopropanol, n-propanol; sulfoxides such as dimethyl sulfoxide; amides such as dimethyl formamide, dimethyl acetamide; ketones such as acetone, methyl ethyl ketone, methyl isobutyl ketone; water and or mixtures thereof. Preferably, the solvent is ethylacetate.

The solvent may be removed by methods known in the art such as centrifugation, filtration, distillation, rotavapour evaporation and the like.

Suitable base may be selected from the group consisting of organic bases or inorganic bases. Inorganic bases may be selected from the group consisting of hydroxides such as sodium hydroxide, potassium hydroxide, calcium hydroxide, lithium hydroxide; carbonate such as of sodium carbonate, potassium carbonate, calcium carbonate, lithium carbonate; alkoxide such as sodium methoxide, potassium methoxide; bicarbonates such as sodium bicarbonate, potassium bicarbonate, lithium bicarbonate; ammonia and the like. Organic bases may be selected from the group consisting of organic amines such as triethylamine, diisopropylethylamine, N,N-dimethylaniline, pyridine, 4-dimethylaminopyridine, N-methylmorpholine.

In one embodiment, the present invention provides the L-pyroglutamate salt of (S)-2-(3-ethoxy-4-methoxyphenyl)-1-(methylsulphonyl)eth-2-ylamine.

In one embodiment, the present invention provides, L-pyroglutamate salt of (S)-2-(3-ethoxy-4-methoxyphenyl)-1-(methyl sulphonyl)eth-2-ylamine characterized by 1HNMR having peaks at 1.32, 1.93-2.29, 2.88, 3.36-3.52, 3.71, 3.96-4.01, 4.335.52, 6.89, 7.05, 7.79.

In one embodiment, the present invention provides L-pyroglutamate salt of (S)-2-(3-ethoxy-4-methoxyphenyl)-1-(methylsulphonyl)eth-2-ylamine characterized by X-ray Diffraction (XRD) spectrum having peak reflections at about 7.25, 12.75, 18.43, 21.78 and 26.67±0.2 degrees 2 theta.

In one embodiment, the present invention provides L-pyroglutamate salt of (S)-2-(3-ethoxy-4-methoxyphenyl)-1-(methyl sulphonyl)eth-2-ylamine characterized by Differential Scanning Calorimetric (DSC) thermogram having endothermic peak at about 182.3±3° C.

In one embodiment, the present invention provides a process for preparation of apremilast comprising reacting the compound of formula II with L-pyroglutamate salt of (S)-2-(3-ethoxy-4-methoxyphenyl)-1-(methylsulphonyl) eth-2-ylamine, wherein the L-pyroglutamate salt of (S)-2-(3-ethoxy-4-methoxyphenyl)-1-(methylsulphonyl)eth-2-ylamine is prepared by a process comprising reacting L-pyroglutamatic acid with 2-(3-ethoxy-4-methoxyphenyl)-1-(methylsulphonyl)eth-2-ylamine.

It was surprisingly noted that the deacetyl impurity, the compound of formula IV, formed during the reaction of compound of formula II with the compound of formula III or salt thereof in the presence of acetic acid was not detected when the reaction was carried out in presence of a non-carboxylic acid solvent.

In one embodiment, the present invention provides a process for the preparation of apremilast, a compound of formula I wherein apremilast was obtained directly from the reaction mixture containing a non-carboxylic acid solvent in high chemical purity without any further purification.

In one embodiment, the present invention provides a process for the preparation of apremilast, a compound of formula I wherein the apremilast is obtained by reacting compound of formula II with a compound of formula III or a salt thereof in presence of acetonitrile. The apremilast obtained was of high chemical purity and did not involve any further purification.

In one embodiment, the present invention provides a process for the preparation of apremilast, a compound of formula I comprising reacting the compound of formula II with compound of formula III or a salt thereof in the presence of a non-carboxylic acid solvent wherein the apremilast was obtained directly from the reaction mixture in a purity of at least 98% as determined by HPLC without purification step.

In one embodiment, the present invention provides a process for the preparation of apremilast, a compound of formula I comprising reacting the compound of formula II with N-acetyl-L-leucine salt of compound of formula III in the presence of acetonitrile wherein the apremilast is obtained directly from the reaction mixture in a purity of at least 98% as determined by HPLC without purification step.

In one embodiment, the present invention provides a process for the preparation of apremilast, a compound of formula I comprising reacting the compound of formula II with L-pyroglutamate salt of compound of formula III in the presence of acetonitrile wherein the apremilast is obtained directly from the reaction mixture in a purity of at least 98% as determined by HPLC without purification step.

In one embodiment, the present invention provides a method of assessing the purity of apremilast by HPLC comprising the steps of:
a) providing a standard solution of deacetyl apremilast; and
b) using the solution as a reference marker to determine the level of deacetyl apremilast impurity.

The determination of the presence of deacetyl apremilast, the compound of formula IV in the sample of apremilast is effected by comparing the retention of the different components of the sample of apremilast by the chromatographic technique with the retention of the compounds of formula IV under the same chromatographic conditions.

The term "reference marker", as used herein, refers to a compound that may be used in qualitative analysis to identify components of a mixture based on their position, and/or in quantitative analysis to determine the concentration of said compound in a mixture by reference to the concentration of a solution comprising a known amount of said component.

In one embodiment, according to the present invention a reference marker solution will comprise deacetyl apremilast dissolved in an appropriate solvent. The method of analysis will be known to a person skilled in the art. Thus, assessing the purity of apremilast, by using deacetyl apremilast as reference marker, according to step (b), means determining the concentration of deacetyl apremilast, respectively. Preferably, the concentration of deacetyl apremilast is determined by means of conventional methods known in the art for quantifying compounds, such as HPLC.

In one embodiment, the present invention provides a process for the preparation of the reference marker deacetyl apremilast, the compound of formula IV comprising reacting apremilast with an acid.

The reaction transpires over a period of about 10 to 20 hours. The deacetyl apremilast may be isolated by methods known in the art such as filtration, centrifugation, distillation and the like.

In one embodiment, the present invention provides deacetyl apremilast, the compound of formula IV characterized by 1HNMR (δ DMSO) having peaks at 1.31, 3.0, 3.72, 3.96-4.06, 4.10-4.11, 4.32-4.41, 5.71-5.73, 6.90, 6.93-7.45.

In one embodiment, the present invention provides apremilast, a compound of formula I wherein the content of deacetyl apremilast compound of formula IV is less than 0.5% w/w with respect to apremilast as determined by HPLC.

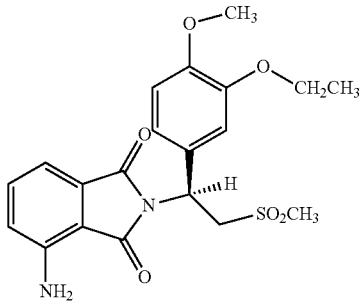

IV

In one embodiment, the present invention provides apremilast, a compound of formula I wherein the content of deacetyl apremilast, compound of formula IV is less than 0.1% w/w with respect to apremilast as determined by HPLC.

In one embodiment, the present invention provides apremilast, a compound of formula I wherein deacetyl apremilast, compound of formula IV is not detected as determined by HPLC.

In one embodiment, the present invention provides use of apremilast, a compound of formula I wherein the content of compound of formula IV is less than 0.5% w/w with respect to apremilast as determined by HPLC for the manufacture of a pharmaceutical composition.

In one embodiment, the present invention provides apremilast a compound of formula I containing deacetyl apremilast compound of formula IV in an amount from about 0.15% w/w to about 0.03% w/w as determined by HPLC.

In one embodiment, the present invention provides a pharmaceutical formulation comprising apremilast a compound of formula I containing deacetyl apremilast compound of formula IV in an amount from about 0.15% w/w to about 0.03% w/w as determined by HPLC and pharmaceutically acceptable excipients.

In one embodiment, the present invention provides a process for the preparation of apremilast comprising:
a) reacting the compound of formula II with a compound of formula III or salt thereof in a non-carboxylic acid solvent;
b) isolating apremilast from the above reaction mixture; and
c) assessing the purity of apremilast by using deacetyl apremilast, the compound of formula IV as a reference marker to determine the level of deacetyl apremilast impurity.

In one embodiment, the present invention provides apremilast xylene solvate.

In one embodiment, the present invention provides apremilast p-xylene hemisolvate.

In one embodiment, the present invention provides apremilast p-xylene hemisolvate characterized by X-ray Diffraction (XRD) spectrum having peak reflections at about 13.15, 14.92, 18.89±0.2 degrees 2 theta.

In one embodiment, the present invention provides apremilast p-xylene hemisolvate characterized by Thermogravimetric Analysis (TGA) thermogram, showing a weight loss of about 9.9% up to 200° C. determined over the temperature range of 30 C-250° C. and heating rate of 10° C. per min.

In one embodiment, the present invention provides apremilast p-xylene hemisolvate characterized by Differential Scanning Calorimetric (DSC) thermogram having endothermic peak at about 139.7±3° C. and 151.0±3° C.

In one embodiment, the present invention provides apremilast p-xylene hemisolvate characterized by 1HNMR (δ DMSO) having peaks at 1.32, 2.19, 2.24, 3.01, 3.73, 3.98-4.04, 4.12-4.17, 4.30-4.34, 5.75-5.79, 6.91-8.45, 9.71.

In one embodiment, the present invention provides process for the preparation of apremilast, a compound of formula I, in amorphous form, the process comprising:
(a) dissolving a solvate of apremilast in a solvent to form a solution; and
(b) removing the solvent from the solution obtained in (a).

In one embodiment, in step (a) of the above process, the solvate is solvate with mixed xylene, p-xylene, p-xylene hemisolvate, dimethyl carbonate solvate.

In one embodiment, in step a) of the above process the solvate of apremilast is dissolved in a solvent selected from the group consisting of water, ketone such as acetone, methyl ethyl ketone, and alcohols like isopropyl alcohol, n-butanol, isobutanol and the like or mixtures thereof.

In one embodiment, in step a) of the above process the solvate of apremilast is dissolved in methyl ethyl ketone.

In one embodiment, in step a) of the above process the p-xylene hemisolvate of apremilast is dissolved in methyl ethyl ketone.

In one embodiment, in step b) of the above process the solvent is removed by rotational distillation, vacuum distillation, spray drying, fluid bed drying, lyophilization, flash drying, spin flash drying, or thin-film drying.

In one embodiment, in step b) of the above process the solvent from the solution containing apremilast is removed by rotational distillation.

In one embodiment, the present invention provides process for the preparation of apremilast, a compound of formula I, in amorphous form, the process comprising:

(a) dissolving a p-xylene hemisolvate of apremilast in a solvent to form a solution; and (b) removing the solvent from the solution obtained in (a).

In one embodiment the present invention provides apremilast dimethyl carbonate solvate.

In one embodiment the present invention provides apremilast dimethyl carbonate solvate characterized by Differential Scanning Calorimetric (DSC) thermogram having endothermic peak at about 121° C.±3° C.

In one embodiment the present invention provides a process for the preparation of apremilast solvate comprising treating apremilast with a solvent and isolating the solvate of apremilast.

As used herein the term "treating" refers to contacting, dissolving, suspending or slurrying apremilast.

In one embodiment, apremilast is dissolved in p-xylene solvent. The solution was cooled and then isolated by methods known in the art such as filtration, centrifugation, distillation and the like.

In one embodiment, the present invention provides pharmaceutical compositions comprising apremilast or salt thereof obtained by the processes herein described, having a $D_{50}$ and $D_{90}$ particle size of less than about 150 microns, preferably less than about 100 microns, more preferably less than about 50 microns, still more preferably less than about 20 microns, still more preferably less than about 15 microns and most preferably less than about 10 microns.

In one embodiment, the present invention provides apremilast obtained by the processes herein described having $D_{90}$ particle size of less than about 16 microns and $D_{50}$ particle size of less than about 8 microns.

The particle size disclosed here can be obtained by, for example, any milling, grinding, micronizing or other particle size reduction method known in the art to bring the solid state apremilast into any of the foregoing desired particle size range.

In one embodiment, the compound of formula II is prepared by a process as depicted schematically:

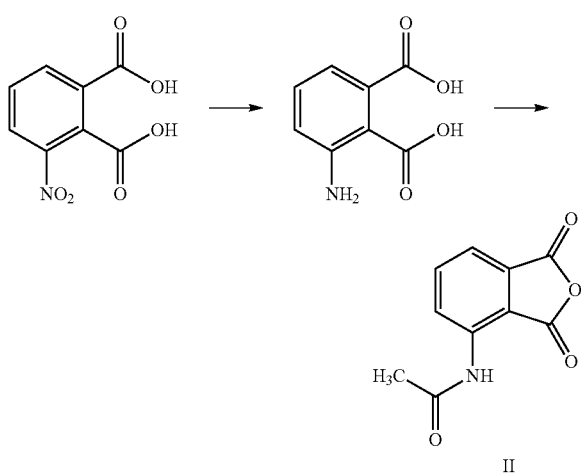

In one embodiment, the compound of formula III or a salt thereof is prepared by a process as depicted schematically:

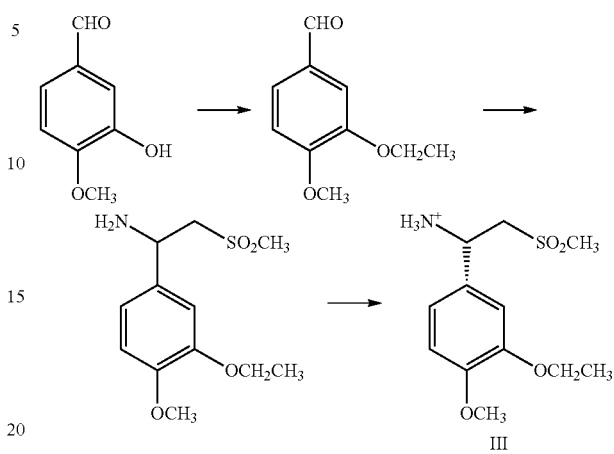

In one embodiment, 3-hydroxy-4-methoxybenzaldehyde is alkylated to obtain 3-ethoxy-4-methoxybenzaldehyde. The product thus obtained is converted to 1-(3-ethoxy-4-methoxyphenyl)-2-methylsulfonylethylamine. This is then resolved to obtain compound of formula III or salt thereof.

In one embodiment, the compound of formula III or salt thereof thus obtained may be subjected to further to purification in a suitable solvent.

Suitable solvent may be selected from the group consisting of water, alcohols such as methanol, ethanol, n-propanol, isopropanol, n-butanol, isobutanol and the like; chlorinated hydrocarbon solvents such as methylene dichloride, ethylene dichloride, chloroform, carbon tetrachloride and the like; esters such as ethyl acetate, butyl acetate and the like; ketones such as acetone, methyl ethyl ketone, isobutyl ketone; nitriles such as acetonitrile, propionitrile; water; amides such as dimethyl formamide, dimethyl acetamide and the like; sulfoxides such as dimethyl sulfoxides and the like; hydrocarbons such as hexane, toluene, xylene, cyclohexane, n-heptane and the like; ethers such as diethyl ether, methyl-tertiary butyl ether, diisopropyl ether, tetrahydrofuran and the like or mixtures thereof.

In one embodiment, the compound of formula III or a salt thereof is purified in methanol or ethanol.

The present invention provides apremilast as characterized and analyzed by following techniques:

HPLC method: High performance liquid chromatography (HPLC) was performed with the conditions described below for detecting purity:

Column: Hypersil BDS, C-18, 150×4.6 mm, Column temperature: 25° C., Mobile phase: A=Buffer, B=Acetonitrile:Methanol (30:70 v/v), 5μ, Diluent: Water:Acetonitrile (20:80 v/v); Flow Rate: 1.0 mL/minute Detection wavelength: UV 230 nm, Injection volume: 10 μL, Buffer: 0.01% Perchloric acid in water.

X-ray powder diffraction profile was obtained using an X-ray Diffractometer (Philips X'Pert Pro, PANalytical). The measurements were carried out with a Pre FIX module programmable divergence slit and anti-scatter Slit (Offset 0.00°); target, Cu; filter, Ni; detector, X'Celerator [1]; Scanning Mode; Active length (2Theta)=2.122°; generator 45 KV; tube current 40 mAmp. The samples were scanned in the full 2θ range of 2-50° with a "time-per-step" 50 seconds.

Instrumental settings for NMR: Proton NMR spectra were recorded in DMSO-$d_6$ using NMR instrument-Varian 300 MHZ.

PSD: PSD analysis performed on Malvern Mastersizer 2000 with Sample handling unit 'Hydro2000S (A) using 0.5% w/v solution of tween 80 in water.

DSC (Mettler Toledo 822e): Temperature range is "30° C. to 350° C." and heating rate is 10° C./minute The following examples are provided to enable one skilled in the art to practice the invention and are merely illustrative of the invention. The examples should not be read as limiting the scope of the invention.

EXAMPLES

Example 1: Preparation of 3-aminophthalic acid 3-nitrophthalic acid (100 gm) and 10% Pd/C (3.2 gm) in ethanol (600 ml) was charged in autoclave and hydrogen pressure of 4.0 kg applied for 3.0 hr at 20-25° C. in autoclave. The reaction mass was cooled to 20° C. and filtered through hyflo bed. The filtrate was distilled under reduced pressure and to the residue acetone was charged. The reaction mass was cooled to 10° C. and followed by addition of conc. hydrochloric acid and stirred. The solvent was removed under reduced pressure and acetonitrile was added. The reaction mass was cooled to 10° C. and precipitated solid was filtered. The product was dried at 45-50° C. under vacuum for 6 hr to obtain 65.0 gm of 3-aminophthalic acid hydrochloride salt.

Example 2: Preparation of 3-acetamidophthalic Anhydride

A stirred solution of 3-aminophthalic acid hydrochloride (65.0 gm) in acetic anhydride (195 ml) was heated to 110° C. and maintained for 2.0 hr. The reaction mass was cooled to 5° C. The product was filtered, washed with cyclohexane and dried at 40° C. for 6.0 hr to obtain 45.0 gm of 3-acetamidophthalic anhydride.

Example 3: Preparation of N-acetyl-L-leucine Salt of (S)-2-(3-ethoxy-4-methoxyphenyl)-1-(methyl sulphonyl)eth-2-ylamine To a stirred solution 1-(3-ethoxy-4-methoxyphenyl)-2-(methyl sulfonyl)ethanamine (2500 gm) in methanol (20.0 lit) was added N-acetyl-L-Leucine (950.0 gm) slowly at 25° C. and then the reaction mixture was heated to reflux temperature and maintained for 1.0 hr. The reaction mass was cooled to 25-30° C. and stirred for 4.0 hr at 25-30° C. The product was filtered and washed with methanol and dried under vacuum at 60° C. for 4.0 hr to obtain 2000.0 gm of crude product. The crude product was subjected to methanol purification to obtain 1670 gm of N-acetyl L-leucine salt of (S)-2-(3-ethoxy-4-methoxyphenyl)-1-(methylsulphonyl) eth-2-ylamine. chiral purity >99.5%.

Example 4: Preparation of (S)-N-{2-(1-(3-ethoxy-4-methoxyphenyl)-2-methylsulphonyl)ethyl)-1,3-dioxo-2,3-dihydro-1H-isoindol-4-yl}acetamide (Apremilast)

A stirred solution of N-acetyl L-leucine salt of (S)-2-(3-ethoxy-4-methoxyphenyl)-1-(methyl sulphonyl)eth-2-ylamine (500.0 gm) and 3-acetamidophthalic anhydride (229.85 gm) in 4.0 lit acetonitrile was refluxed for 3.0 hr and then cooled to 50° C. The solvent was removed under reduced pressure to obtain a semisolid residue. To the residue water was added and pH adjusted to 7-8 using saturated sodium bicarbonate solution. The product was extracted into ethyl acetate and the solvent was removed under reduced pressure to obtain apremilast. HPLC purity: 99%

The apremilast thus obtained was heated at 60-65° C. in a solvent mixture of acetone and ethanol to get clear solution. The reaction mixture was cooled to 25-30° C. and stirred for 12 hr. The precipitated product was filtered and washed with ethanol and dried at 60° C. under vacuum for 12.0 hr to obtain 425.0 gm of (S)-N-{2-(1-(3-ethoxy-4-methoxyphenyl)-2-methylsulphonyl)ethyl)-1,3-dioxo-2,3-dihydro-1H-isoindol-4-yl}acetamide. HPLC purity 100.0%, R isomer <0.5%, S-isomer >99.5%.

Comparison Data of Example 4 and Example 15

| Example | Solvent | HPLC purity | Deacetyl Impurity |
| --- | --- | --- | --- |
| Example 15 | Acetic acid | 98.46% | 1.07% |
| Example 4 | Acetonitrile | 100.0% | Nil |

Example 5: Preparation of Deacetyl Apremilast

To stirred solution of conc hydrochloric acid (30 ml) and methanol (60 ml), (S)-N-{2-(1-(3-ethoxy-4-methoxyphenyl)-2-methylsulphonyl)ethyl)-1,3-dioxo-2,3-dihydro-1H-isoindol-4-yl}acetamide (apremilast) (10 gm) was added and stirred overnight. The solvent was distilled under reduced pressure and water was added to the reaction mixture and stirred, the product was filtered and washed with water. The pH was adjusted to 7-8 using saturated aqueous sodium bicarbonate and stirred. The precipitated product was washed with water dried at 55° C. for 6.0 hr to obtain 8 gm of 4-amino-2-[(1S)-1-(3-ethoxy 4-methoxyphenyl)-2-methanesulfonylethyl]-2,3-dihydro-1H-isoindole-1,3-dione. HPLC purity 99.7%.

Example 6: Preparation of (S)-N-{2-(1-(3-ethoxy-4-methoxyphenyl)-2-methylsulphonyl)ethyl)-1,3-dioxo-2,3-dihydro-1H-isoindol-4-yl}acetamide A solution of (S)-2-(3-ethoxy-4-methoxyphenyl)-1-(methylsulphonyl)eth-2-ylamine-N-acetyl-L-leucine salt (2.0 gm) and 3-acetamidophthalic anhydride (0.92 gm) in acetone (10.0 ml) and ethanol (10.0 ml) was refluxed for 15.0 hr and then cooled to 50° C. The solvent was removed under reduced pressure to obtain a residue. The residue was treated with water and sodium bicarbonate and product was extracted into ethyl acetate. The solvent was removed under reduced pressure to obtain residue. The above residue was heated in a mixture of acetone and ethanol at 55-60° C. and maintained for 30.0 min. The reaction mass was cooled to 25-30° C. and stirred for 12.0 hr. The precipitated product was filtered and dried at 60° C. under vacuum for 12.0 hr to obtain 0.8 gm of (S)-N-{2-(1-(3-ethoxy-4-methoxyphenyl)-2-methylsulphonyl)ethyl)-1,3-dioxo-2,3-dihydro-1H-isoindol-4-yl}acetamide. HPLC purity >99.8%.

Example 7: Preparation of (S)-N-{2-(1-(3-ethoxy-4-methoxyphenyl)-2-methylsulphonyl)ethyl)-1,3-dioxo-2,3-dihydro-1H-isoindol-4-yl}acetamide A solution of N-acetyl-L-leucine salt of (S)-2-(3-ethoxy-4-methoxyphenyl)-1-(methyl sulphonyl)eth-2-ylamine (2.0 gm) and 3-acetamidophthalic anhydride (0.92 gm) in dimethyl formamide (20.0 ml) was heated to 75-80° C. for 15.0 hr and then cooled to 25° C. To the reaction mass water was added. The precipitated product was filtered washed with water and dried at 60° C. for 6.0 hr to obtain 1.2 gm of product. The product was dissolved in a mixture of acetone and ethanol at 60-65° C. and maintained for 30.0 min. The reaction mass was cooled to 25-30° C. and stirred for 12.0 hr, the precipitated product was filtered, dried at 60° C. under vacuum for 12.0 hr to obtain 0.8 gm of (S)-N-{2-(1-(3-ethoxy-4-methoxyphenyl)-2-ethyl sulphonyl)ethyl)-1,3-dioxo-2,3-dihydro-1H-isoindol-4-yl}acetamide. HPLC purity 100.0%.

Example 8: Preparation of (S)-N-{2-(1-(3-ethoxy-4-methoxyphenyl)-2-methylsulphonyl)ethyl)-1,3-dioxo-2,3-dihydro-1H-isoindol-4-yl}acetamide A stirred solution of N-acetyl-L-leucine salt of (S)-2-(3-ethoxy-4-methoxyphenyl)-1-(methylsulphonyl)eth-2-ylamine (2.0 gm) and 3-acetamidophthalic anhydride (0.92 gm) in 20.0 ml methyl ethyl ketone was refluxed for 15.0 hr and then cooled to 50° C. The solvent was removed under reduced pressure and the residue washed with water and saturated aqueous sodium bicarbonate solution. The product was extracted with ethyl acetate and the organic layer washed with water and brine and dried over sodium sulphate. The solvent was removed under reduced pressure to obtain residue. The above residue was taken in a mixture of acetone and ethanol and heated to 55-60° C. The reaction mass was maintained for 30.0 min and slowly cooled to 25-30° C. and stirred for 12.0 hr, the precipitated product was filtered and dried at 60° C. under vacuum for 12.0 hr to obtain 0.8 gm of (S)-N-{2-(1-(3-ethoxy-4-methoxyphenyl)-2-methylsulphonyl)ethyl)-1,3-dioxo-2,3-dihydro-1H-isoindol-4-yl}acetamide. HPLC purity >99.9%

Example 9: Preparation of (S)-N-{2-(1-(3-ethoxy-4-methoxyphenyl)-2-methylsulphonyl)ethyl)-1,3-dioxo-2,3-dihydro-1H-isoindol-4-yl}acetamide A stirred solution of (S)-2-(3-ethoxy-4-methoxyphenyl)-1-(methylsulphonyl)eth-2-ylamine-N-acetyl-L-leucine salt (2.0 gm) and 3-acetamidophthalic (0.92 gm) in 20.0 ml water was refluxed for 15.0 hr and then cooled to 25° C. The reaction mass was treated with aqueous sodium bicarbonate solution. The product was extracted in ethyl acetate. The organic layer was washed with water and brine and dried over sodium sulphate. The solvent was removed under reduced pressure to obtain residue. The above residue was taken in a mixture of acetone and ethanol and heated to 55-60° C. and maintained for 30.0 min. The reaction mixture was cooled to 25-30° C. and stirred for 12.0 hr. The precipitated product was filtered and dried at 60.0° C. under vacuum for 12.0 hr to obtain 0.65 gm of (S)-N-{2-(1-(3-ethoxy-4-methoxyphenyl)-2-methylsulphonyl)ethyl)-1,3-dioxo-2,3-dihydro-1H-isoindol-4-yl}acetamide. HPLC purity >99.5%

Example 10: Preparation of (S)-N-{2-(1-(3-ethoxy-4-methoxyphenyl)-2-methylsulphonyl) ethyl)-1,3-dioxo-2,3-dihydro-1H-isoindol-4-yl}acetamide A stirred solution of (S)-2-(3-ethoxy-4-methoxyphenyl)-1-(methylsulphonyl)eth-2-ylamine-N-acetyl-L-leucine salt (2.0 gm) and 3-acetamidophthalic anhydride (0.92 gm) in tetrahydrofuran (10.0 ml) and water (10.0 ml) was refluxed for 15.0 hr and then cooled to 50° C. The solvent was removed under reduced pressure to obtain residue. The above residue was treated with water and saturated aqueous sodium bicarbonate solution and product extracted with ethyl acetate. The solvent was removed under reduced pressure to obtain residue. The residue thus obtained was treated with a mixture of acetone and ethanol and heated to 55-60° C. and maintained for 30.0 min. The reaction mixture was slowly cooled to 25-30° C. and stirred for 12.0 hr. The precipitated product was filtered and dried at 60° C. under vacuum for 12.0 hr to obtain 0.810 gm of (S)-N-{2-(1-(3-ethoxy-4-methoxyphenyl)-2-methyl sulphonyl) ethyl)-1,3-dioxo-2,3-dihydro-1H-isoindol-4-yl}acetamide. HPLC purity >98.8%.

Example 11: Preparation of (S)-N-{2-(1-(3-ethoxy-4-methoxyphenyl)-2-methylsulphonyl)ethyl)-1,3-dioxo-2,3-dihydro-1H-isoindol-4-yl}acetamide A stirred solution of (S)-2-(3-ethoxy-4-methoxyphenyl)-1-(methyl sulphonyl)eth-2-ylamine-N-acetyl-L-leucine salt (2.0 gm) and 3-acetamidophthalic anhydride (0.92 gm) in tetrahydrofuran (20.0 ml) was refluxed for 15.0 hr and then cooled to 50° C. and the solvent was removed under reduced pressure. The residue obtained was treated with saturated aqueous sodium bicarbonate solution and product extracted with ethyl acetate. The solvent was removed under reduced pressure and to the residue a mixture acetone and ethanol was added and heated to 55-60° C. This was maintained for 30.0 min and slowly cooled to 25-30° C. and further stirred for 12.0 hr. The precipitated product was filtered and dried at 60° C. under vacuum for 12.0 hr to obtain 1.0 gm of (S)-N-{2-(1-(3-ethoxy-4-methoxyphenyl)-2-methyl sulphonyl)ethyl)-1,3-dioxo-2,3-dihydro-1H-isoindol-4-yl}acetamide. HPLC purity: 100.0%

Example 12: Preparation of (S)-N-{2-(1-(3-ethoxy-4-methoxyphenyl)-2-methylsulphonyl)ethyl)-1,3-dioxo-2,3-dihydro-1H-isoindol-4-yl}acetamide A stirred solution of (S)-2-(3-ethoxy-4-methoxyphenyl)-1-(methyl sulphonyl)eth-2-ylamine-N-acetyl-L-leucine salt (1.0 gm) and 3-acetamidophthalic anhydride (0.46 gm) in toluene (20.0 ml) was refluxed for 24.0 hr and then cooled to 50° C. To the reaction mixture water and saturated sodium bicarbonate was added and product extracted with ethyl acetate and the solvent was removed under reduced pressure to obtain residue. To this residue a mixture of acetone and ethanol was added and maintained for 120.0 min at 25-30° C. The precipitated product was filtered and dried at 60° C. under vacuum for 6.0 hr to obtain 0.57 gm of (S)-N-{2-(1-(3-ethoxy-4-methoxyphenyl)-2-methyl sulphonyl)ethyl)-1,3-dioxo-2,3-dihydro-1H-isoindol-4-yl}acetamide. HPLC purity >99.6%.

Example 13: Preparation of L(−)-pyroglutamate Salt of (S)-2-(3-ethoxy-4-methoxyphenyl)-1-(methyl sulfonyl) ethanamine To a stirred solution of 1-(3-ethoxy-4-methoxyphenyl)-2-(methyl sulfonyl)ethanamine (41.6 gm) in methanol (500.0 ml) was added L(−)-pyroglutamic salt acid (19.67 gm) slowly at 25-30° C. The reaction mixture was heated to reflux temperature and maintained for 1.0 hr then slowly cooled the reaction mass to 25-30° C. over a period of 2.0 hr and stirred for 1.0 hr. The product was filtered, washed with methanol and dried under vacuum at 60° C. for 4.0 hr to obtain L(−)-pyroglutamate salt of (S)-2-(3-ethoxy-4-methoxyphenyl)-1-(methylsulfonyl)ethanamine (24.0 gm). Chiral purity: 99.94%.

Example 14: Preparation of (S)-N-{2-(1-(3-ethoxy-4-methoxyphenyl)-2-methylsulphonyl)ethyl)-1,3-dioxo-2,3-dihydro-1H-isoindol-4-yl}acetamide A stirred solution of L-pyroglutamate salt of (S)-2-(3-ethoxy-4-methoxyphenyl)-1-(methylsulfonyl) ethanamine (15 gm) and 3-acetamidophthalic anhydride (7.64 gm) in acetonitrile (150.0 ml) was refluxed for 4.0 hrs and then cooled to 50° C. The solvent was removed under reduced pressure to obtain semisolid residue. To the residue water was added and pH adjusted to 7-8 with saturated aqueous sodium bicarbonate solution. The product was extracted into ethyl acetate and the solvent was removed under reduced pressure. The residue was treated with a mixture of acetone and ethanol and heated to 60-65° C. to get clear solution. The reaction mass was cooled to 25-30° C. and stirred for 12 hr. The precipitated product was filtered and washed with ethanol and dried at 60° C. under vacuum for 4.0 hr to obtain (S)-N-{2-(1-(3-ethoxy-4-methoxyphenyl)-2-methylsulphonyl)ethyl)-1,3-dioxo-2,3-dihydro-1H-isoindol-4-yl}acetamide (13.1 gm). Chemical purity: 99.93%, Chiral Purity: 99.90%.

Example 15: Preparation of (S)-N-{2-(1-(3-ethoxy-4-methoxyphenyl)-2-methylsulphonyl)ethyl)-1,3-dioxo-2,3-dihydro-1H-isoindol-4-yl}acetamide Comparative Example In a 500.0 ml 3-necked round bottom flask (S)-2-(3-ethoxy-4-methoxyphenyl)-1-(methylsulfonyl)eth-2-yl amine N-acetyl-L-leucine salt (25.0 gm) and 3-acetamidophthalic anhydride (12.1 gm) and glacial acetic acid (250.0 ml) were charged. The mixture was refluxed overnight and then cooled to 50° C. The solvent was removed in vacuum and the residue was dissolved in ethyl acetate (250.0 ml). The resulting solution was washed with water, saturated aqueous sodium bicarbonate, brine and dried over sodium sulphate. The solvent was removed under vacuum and residue recrystallized from a binary solvent containing ethanol and acetone. The solid was isolated by vacuum filtration and washed with ethanol. The product was dried in vacuum at 60° C. to obtain 15.5 gm title product.

Example 16: Synthesis of L-pyroglutamate salt of (S)-2-(3-ethoxy-4-methoxyphenyl)-1-(methylsulphonyl)eth-2-ylamine A stirred solution 1-(3-ethoxy-4-methoxyphenyl)-2-(methylsulfonyl)ethanamine (50 gm) in 1500 ml ethanol was added L-pyroglutamic acid (23.62 g) at 25-30° C. Then reaction mixture was heated to reflux temperature and stirred for 30 min. Slowly cool the reaction mass to room temperature. Stirred for 12 hr at ambient temperature. The slurry was filtered and wet cake was washed with ethanol. Dry the wet cake under vacuum at 50-55° C. for 4.0 hr. The crude solid (35 g) and ethanol (1155 ml) were heated to reflux for 30 min, slowly cool the reaction mass to room temperature and stirred for additional 12.0 hr at ambient temperature. The slurry was filtered and wet cake was washed with ethanol. The wet cake was dried under vacuum at 50-55° C. yielding 29.7 g of L-Pyroglutamic acid salt of (S)-2-(3-ethoxy-4-methoxyphenyl)-1-(methylsulfonyl) ethanamine. Chiral purity: 99.9%. Chemical Purity: 99.5% IH NMR δ DMSO 1.32, 1.93-2.29, 2.88, 3.36-3.52, 3.71, 3.96-4.01, 4.335.52, 6.89, 7.05, 7.79

XRD of L-Pyroglutamic acid salt of (S)-2-(3-ethoxy-4-methoxyphenyl)-1-(methylsulfonyl) ethanamine

| Pos. [°2Th.] | d-spac [Å] | Rel. Int. [%] |
| --- | --- | --- |
| 6.35 | 13.91 | 0.50 |
| 7.0 | 12.61 | 21.28 |
| 7.25 | 12.18 | 100.00 |
| 11.28 | 7.84 | 9.72 |
| 12.75 | 6.94 | 22.33 |
| 14.01 | 6.31 | 4.03 |
| 14.50 | 6.10 | 1.19 |
| 16.95 | 5.23 | 3.91 |
| 17.67 | 5.01 | 5.27 |
| 18.42 | 4.81 | 56.13 |
| 18.86 | 4.70 | 4.42 |
| 19.16 | 4.63 | 15.90 |
| 21.06 | 4.21 | 3.79 |
| 21.78 | 4.08 | 21.08 |
| 22.62 | 3.92 | 6.43 |
| 23.55 | 3.77 | 15.79 |
| 24.48 | 3.63 | 1.88 |
| 24.79 | 3.59 | 4.96 |
| 25.50 | 3.49 | 5.33 |
| 26.13 | 3.40 | 2.79 |
| 26.66 | 3.34 | 19.17 |
| 27.52 | 3.24 | 2.02 |
| 28.20 | 3.16 | 3.63 |
| 29.19 | 3.05 | 5.50 |
| 29.43 | 3.03 | 3.69 |
| 29.88 | 2.98 | 3.41 |
| 30.21 | 2.95 | 11.42 |

Example 17 Synthesis of of (S)-N-{2-(1-(3-ethoxy-4-methoxyphenyl)-2-methylsulphonyl)ethyl)-1,3-dioxo-2,3-dihydro-1H-isoindol-4-yl}acetamide p-xylene hemisolvate A stirred solution of L-pyroglutamic acid salt of (S)-2-(3-ethoxy-4-methoxyphenyl)-1-(methylsulfonyl) ethanamine (25 gm), and 3-acetamidophthalic anhydride (12.75 gm) in 375 ml acetonitrile was refluxed for 4.0 hr. Then cooled to 50° C. and the solvent was removed under reduced pressure to obtain residue. To the residue was added water and saturated aqueous sodium bicarbonate solution and extracted with ethyl acetate. The organic layer was dried over sodium sulphate and filtered the organic layer and charged 300 ml of p-xylene to the ethyl acetate layer. This was heated to 80-85° C. to get clear solution. The reaction mixture was cooled to 25-30° C. and stirred for 2 hr. The precipitated product was filtered, washed with p-xylene and dried at 65-70° C. under vacuum for 12 hr to obtain 23.0 gm of (S)-N-{2-(1-(3-ethoxy-4-methoxyphenyl)-2-methylsulphonyl)ethyl)-1,3-dioxo-2,3-dihydro-1H-isoindol-4-yl}acetamide P-xylene hemisolvate, HPLC purity: 99.5%, xylene content: 0.23%. H[1] NMR Data δ DMSO 1.32, 2.19, 2.24, 3.01, 3.73, 3.98-4.04, 4.12-4.17, 4.30-4.34, 5.75-5.79, 6.91-8.45, 9.71.

XRD of P-xylene Hemisolvate

| Pos [°2Th.] | d-spac [Å] | Rel. Int. [%] | Pos. [°2Th.] | d-spac [Å] | Rel. Int. [%] | Pos. [°2Th.] | d-spac [Å] | Rel. Int. [%] |
| --- | --- | --- | --- | --- | --- | --- | --- | --- |
| 7.34 | 12.03 | 100 | 16.12 | 5.5 | 50.25 | 21.41 | 4.15 | 21.36 |
| 9.05 | 9.77 | 15.86 | 16.68 | 5.31 | 2.63 | 22.02 | 4.03 | 33.12 |
| 9.43 | 9.37 | 33.62 | 17.52 | 5.06 | 56.38 | 22.54 | 3.94 | 7.79 |

-continued

| Pos [°2Th.] | d-spac [Å] | Rel. Int. [%] | Pos. [°2Th.] | d-spac [Å] | Rel. Int. [%] | Pos. [°2Th.] | d-spac [Å] | Rel. Int. [%] |
|---|---|---|---|---|---|---|---|---|
| 9.90 | 8.92 | 4.39 | 17.98 | 4.93 | 13.71 | 23.07 | 3.85 | 17.71 |
| 11.34 | 7.8 | 64.6 | 18.89 | 4.69 | 14.54 | 23.48 | 3.78 | 6.34 |
| 12.23 | 7.23 | 23.28 | 19.31 | 4.59 | 8.94 | 23.73 | 3.74 | 6.94 |
| 13.15 | 6.73 | 7.69 | 19.55 | 4.53 | 6.18 | 24.13 | 3.68 | 7.45 |
| 13.68 | 6.47 | 20.76 | 19.86 | 4.46 | 13.8 | 24.47 | 3.63 | 28.14 |
| 13.93 | 6.35 | 4.45 | 20.27 | 4.37 | 13.29 | 24.91 | 3.57 | 18.51 |
| 14.92 | 5.93 | 31.19 | 20.96 | 4.23 | 18.12 | 25.85 | 3.44 | 68.81 |

Example 18: Synthesis of Amorphous (S)-N-{2-(1-(3-ethoxy-4-methoxyphenyl)-2-methylsulphonyl)ethyl)-1,3-dioxo-2,3-dihydro-1H-isoindol-4-yl}acetamide The p-xylene hemisolvate (23.0 gm) of apremilast was taken in methyl ethyl ketone (230 ml) and heated to 60-65° C. to get clear solution. The solvent was removed in rota vapour under reduced pressure to obtained oily residue. The oily residue was dissolved in methyl ethyl ketone (230 ml) and solvent was removed under reduced pressure to obtained oily residue. This process was repeated two times to get 19.0 gm of amorphous apremilast. HPLC purity 99.9%. H¹ NMR Data δ DMSO 1.32, 2.19, 3.01, 3.73, 4.00-4.02, 4.12-4.17, 4.30-4.35, 5.76, 6.96-8.45, 9.71.

Example 19: Synthesis of (S)-N-{2-(1-(3-ethoxy-4-methoxyphenyl)-2-methylsulphonyl)ethyl)-1,3-dioxo-2,3-dihydro-1H-isoindol-4-yl}acetamide Dimethyl carbonate Solvate A stirred solution of N-acetyl-L-leucine salt of (S)-2-(3-ethoxy-4-methoxyphenyl)-1-(methylsulfonyl) ethanamine. (5 gm) and 3-acetamidophthalic anhydride (2.34 gm) in 50 ml acetonitrile was refluxed for 2.0 hr and then cooled to 50° C. and the solvent was removed under reduced pressure to obtain semisolid residue and to the residue was added water and saturated aqueous sodium bicarbonate solution. This was extracted with ethyl acetate and again washed with water and brine. The ethyl acetate was distilled under vacuum to obtain oily residue. To the residue was charged 25 ml of dimethyl carbonate and heated to 85-90° C. to get clear solution then slowly cooled the reaction mixture to 25-30° C. and stirred for 2 hr. The precipitated product was filtered and dried at 70° C. under vacuum for 6 hr to obtain 3.0 gm of (S)-N-{2-(1-(3-ethoxy-4-methoxyphenyl)-2-methylsulphonyl)ethyl)-1,3-dioxo-2,3-dihydro-1H-isoindol-4-yl}acetamide dimethyl carbonate solvate. H¹ NMR Data δ DMSO 1.32, 2.19, 3.02, 3.69, 3.73, 3.98-4.05, 4.13-4.18, 4.31-4.34, 5.77-5.80, 6.92-8.45, 9.71. DSC endotherm: 121° C.±3° C., TGA Loss—9.2% up to 150° C.

Example 20: Preparation of (S)-N-{2-(1-(3-ethoxy-4-methoxyphenyl)-2-methylsulphonyl)ethyl)-1,3-dioxo-2,3-dihydro-1H-isoindol-4-yl}acetamide A stirred solution of L-pyroglutamate salt of (S)-2-(3-ethoxy-4-methoxyphenyl)-1-(methylsulfonyl) ethanamine (10 gm) and 3-acetamidophthalic anhydride (5.1 gm) in acetonitrile (150.0 ml) was refluxed at 80-85° C. The solvent was removed under reduced pressure to obtain semisolid residue. To the residue ethyl acetate and water was added and pH adjusted to 7-8 with saturated aqueous sodium bicarbonate solution. The ethyl acetate layer was separated and washed with brine. The ethyl acetate layer was distilled under vacuum. To the residue was added a mixture of acetone (25 ml) and ethanol (25 ml) and heated to 60-65° C. to get clear solution. The reaction mass was cooled to 15-20° C. and stirred for about 30 min. The product was filtered and washed with ethanol and dried at 60-65 C.° under vacuum for 8.0 hr to obtain (S)-N-{2-(1-(3-ethoxy-4-methoxyphenyl)-2-methylsulphonyl)ethyl)-1,3-dioxo-2,3-dihydro-1H-isoindol-4-yl}acetamide (9.5 gm). Chemical purity: 99.93%, Chiral Purity: 99.90%.

Example 21: Preparation of 3-aminophthalic acid 3-nitrophthalic acid (100 gm) and 10% Pd/C (3 gm) in tetrahydrofuran (100 ml) was charged in autoclave and hydrogen pressure of 2-3 kg/cm² for 3.0 hr at 20-25° C. in autoclave. The reaction mass was cooled to 20° C. and filtered through hyflo bed. To the filtrate was added 180 gm of 20-25% IPA.HCl and cooled to 20° C. and solid was filtered. The product was dried at 45-50° C. under vacuum for 8 hr to obtain 65.0 gm of 3-aminophthalic acid hydrochloride salt.

The invention claimed is:

1. A process for the preparation of apremilast, a compound of formula I

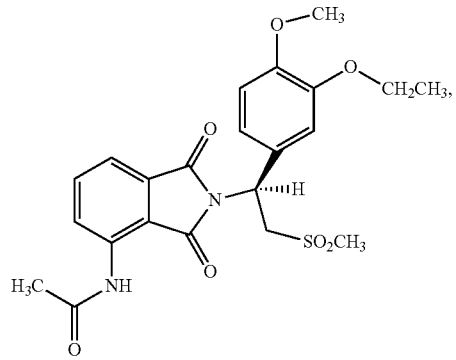

the method comprising reacting a compound of formula II with a compound of formula III or a salt thereof

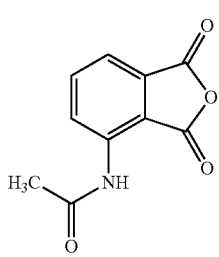

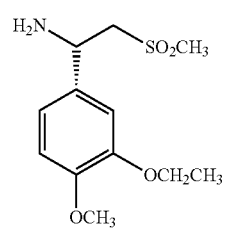

-continued

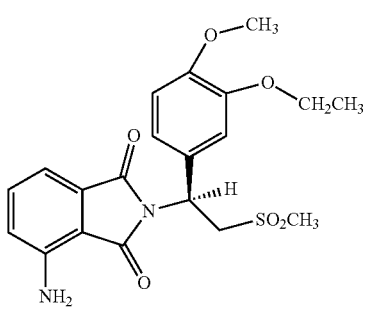

IV in the presence of a non-carboxylic acid solvent to obtain apremilast wherein the content of deacetyl apremilast, a compound of formula IV, is less than 1% w/w as determined by HPLC.

2. The process as claimed in claim 1, wherein the reaction of the compound of formula II with the compound of formula III or a salt thereof is carried out in the absence of acetic acid.

3. The process as claimed in claim 1, wherein the non-carboxylic acid solvent is selected from the group consisting of an alcohol, ketone, hydrocarbon, halogenated hydrocarbon, amide, sulfoxide, ether, ester, nitrile, water and mixtures thereof.

4. The process as claimed in claim 3, wherein the nitrile solvent is acetonitrile.

5. The process as claimed in claim 3, wherein the amide solvent is selected from the group consisting of dimethylformamide (DMF), dimethyl acetamide and formamide.

6. The process as claimed in claim 3, wherein the ketone solvent is selected from the group consisting of acetone, methyl ethyl ketone and methyl isobutylketone.

7. The process as claimed in claim 1, wherein the non-carboxylic acid solvent is water.

8. The process as claimed in claim 1, wherein the salt of the compound of formula III is a salt selected from an optically active acid or chiral amino acid.

9. The process as claimed in claim 8, wherein the optically active acid is selected from the group consisting of mandelic acid, tartaric acid, camphor sulfonic acid, dibenzoyltartaric acid, di-p-toluoyl tartaric acid, malic acid, aspartic acid, mucic acid, pyroglutamic acid, glucoronic acid, camphoric acid, gluconic acid, lactic acid, pantothenic acid, phenyl-propionic acid and diacetyl tartaric acid.

10. The process as claimed in claim 8, wherein the chiral amino acid is selected from the group consisting of alanine, arginine, aspartic acid, glutamine, glutamic acid, glycine, isoleucine, leucine, phenylalanine, proline, serine, valine, 4-aminobutyric acid, 2-amino isobutyric acid, 3-amino propionic acid, norleucine, norvaline, hydroxyproline, cysteic acid, t-butylglycine, t-butylalanine, phenylglycine, cyclohexylalanine, N-acetylphenyl alanine and N-acetyl-leucine.

11. The process as claimed in claim 1, wherein the content of deacetyl apremilast, the compound of formula IV

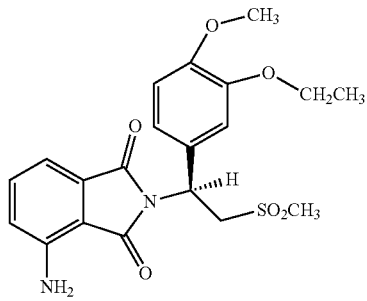

IV is less than 0.5% w/w with respect to apremilast as determined by HPLC.

12. The process as claimed in claim 1, wherein the salt of the compound of formula III is L-pyroglutamate salt of (S)-2-(3-ethoxy-4-methoxyphenyl)-1-(methyl sulphonyl) eth-2-ylamine.

13. The process as claimed in claim 12, wherein the L-pyroglutamate salt of (S)-2-(3-ethoxy-4-methoxyphenyl)-1-(methylsulphonyl)eth-2-ylamine is prepared by a process comprising reacting L-pyroglutamatic acid with 2-(3-ethoxy-4-methoxyphenyl)-1-(methylsulphonyl)eth-2-ylamine.

14. L-pyroglutamate salt of (S)-2-(3-ethoxy-4-methoxyphenyl)-1-(methylsulphonyl)eth-2-ylamine characterized by 1HNMR having peaks at 1.32, 1.93-2.29, 2.88, 3.36-3.52, 3.71, 3.96-4.01, 4.335.52, 6.89, 7.05, and 7.79, and a chiral purity of 99.94%.

15. Apremilast, a compound of formula I,

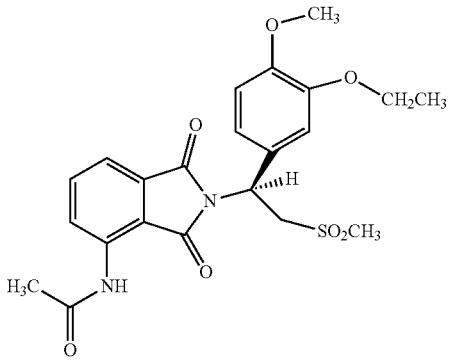

I

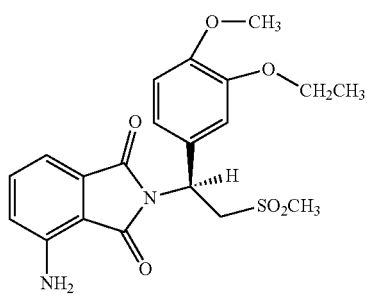

IV having a content of deacetyl apremilast, a compound of formula IV in an amount from aboutn 0.15% w/w to about 0.03% w/w as determined by HPLC.

* * * * *